(12) United States Patent
Eaton et al.

(10) Patent No.: US 11,351,138 B2
(45) Date of Patent: Jun. 7, 2022

(54) COMPOSITION FOR USE IN THE TREATMENT OF EPILEPSY

(71) Applicants: VITAFLO INTERNATIONAL LTD, UK-Liverpool Merseyside (GB); UCL BUSINESS PLC., London (GB)

(72) Inventors: Simon Eaton, London (GB); Simon Heales, Maidenhead (GB); Aziza Khabbush, Woking (GB); Maura Louise ODonnell, Hightown (GB); Patricia Rutherford, Liverpool (GB); Matthew Walker, London (GB); Robin Simon Brooke Williams, Egham (GB)

(73) Assignees: VITAFLO INTERNATIONAL LTD, UK-Liverpool Merseyside (GB); UCL BUSINESS LTD, London (GB)

( * ) Notice: Subject to any disclaimer, the term of this patent is extended or adjusted under 35 U.S.C. 154(b) by 154 days.

(21) Appl. No.: 16/603,713

(22) PCT Filed: Apr. 9, 2018

(86) PCT No.: PCT/EP2018/059031
§ 371 (c)(1),
(2) Date: Oct. 8, 2019

(87) PCT Pub. No.: WO2018/189113
PCT Pub. Date: Oct. 18, 2018

(65) Prior Publication Data
US 2020/0147025 A1    May 14, 2020

(30) Foreign Application Priority Data
Apr. 10, 2017   (EP) .................................... 17165690

(51) Int. Cl.
*A61K 31/20*   (2006.01)
*A23L 33/00*   (2016.01)
*A61P 25/08*   (2006.01)

(52) U.S. Cl.
CPC .............. *A61K 31/20* (2013.01); *A23L 33/30* (2016.08); *A61P 25/08* (2018.01)

(58) Field of Classification Search
CPC .......... A61K 31/20; A23L 33/00; A61P 25/08
See application file for complete search history.

(56) References Cited

FOREIGN PATENT DOCUMENTS

| EP | 2351491 A1 | 8/2011 |
|----|------------|--------|
| WO | 2013186570 | 12/2013 |

OTHER PUBLICATIONS

Hanada (J. of Receptor, Ligand and Channel Research (2014):7. 39-50).*
Chang et al. "Seizure control by ketogenic diet-associated medium chain fatty acids" Neuropharmacology, 2013, vol. 69, pp. 105-114.
Chang et al. "Seizure control by decanoic acid through direct AMPA receptor inhibition" Brain, 2016, vol. 139, pp. 431-443.
Sergeev, "Short Course of Molecular Pharmacology", 1975, p. 10.
Kholodov et al., "Clinical Pharmacokinetics", 1985, pp. 83-98, 134-138, 160 and 378-380.
Vengerovsky, "Pharmacological Incompatibility", Bulletin of Siberian Medicine, Issue No. 3, 2003, pp. 49-56.
Russia Patent Office Action for Application No. 2019135829, dated May 26, 2021, 21 Pages.
Hughes et al.,"The Ketogenic Diet Component Decanoic Acid Increases Mitochondrial Citrate Synthase and Complex 1 Activity in Neuronal Cells", Journal of Neurochemistry, vol. 129, 2014, pp. 426-433.
Japan Patent Office Communication for Application No. P2019-555489, Dispatch No. 857792, Dispatch Date Dec. 21, 2021, 8 pages.

* cited by examiner

*Primary Examiner* — Shirley V Gembeh
(74) *Attorney, Agent, or Firm* — K&L Gates LLP

(57) ABSTRACT

A composition comprising a decanoic acid to octanoic acid ratio of 70:30 to 90:10 wt/wt for use in treating epilepsy or controlling epileptic seizures.

17 Claims, 2 Drawing Sheets

COMPOSITION FOR USE IN THE TREATMENT OF EPILEPSY

FIELD OF THE INVENTION

The present invention generally relates to compositions for treating disorders involving the AMPA receptor. In particular, the present invention provides compositions for treating epilepsy.

BACKGROUND TO THE INVENTION

Epilepsy covers a broad range of neurological disorders that are characterised by seizures. Seizures result from abnormal neuronal activity and manifest in a number of ways, including convulsions and loss of awareness. In many cases epilepsy can be managed by the use of anti-convulsive medication. However for a proportion of patients with epilepsy, treatment with conventional drugs can have minimal effect upon seizure activity. Although surgery is an option for treating patients suffering from certain seizures, for many individuals successful management can be achieved less invasively with the ketogenic diet.

The medium chain triglyceride (MCT) ketogenic diet was first identified as a treatment for refractory epilepsy in 1971. It has provided one of the most effective therapeutic approaches for children with drug resistant epilepsy (Liu, Epilepsia 2008; 49 Suppl. 8: 33-36) and has been demonstrated to be effective in childhood epilepsy in a randomised control trial (Neal et al., Epilepsia 2009; 50: 1109-1117). However, the diet has adverse gastro-intestinal related side effects, such as diarrhoea, vomiting, bloating, and cramps (Liu, Epilepsia 2008; 49 Suppl 8: 33-36.). Furthermore, it has also been shown that there is a high attrition rate for the diet, due to many patients finding the diet difficult to tolerate (Levy et al., Cochrane Database Syst Rev 2012; 3: CD001903).

Ketogenic diets have a high fat and low carbohydrate content with sufficient protein for growth and repair. Ketogenic diets function by forcing the body to metabolise fat instead of carbohydrate as its energy source. Under low dietary carbohydrate conditions, fats are broken down into fatty acids and ketone bodies in the liver, and these compounds are utilised in further metabolic pathways for generating adenosine triphosphate (ATP) as a chemical energy source.

Although ketone bodies resulting from the ketogenic diet have been postulated to play a therapeutic role, seizure control is poorly correlated with ketone body levels (Likhodii et al., Epilepsia 2000; 41: 1400-1410; Thavendiranathan et al., ExpNeurol 2000; 161: 696-703). In addition to ketones, the diet also causes an increase in plasma levels of the two fatty acids provided in MCT oil, the straight chain, ten carbon decanoic acid, and the eight carbon octanoic acid (Haidukewych et al., Clin Chem 1982; 28: 642-645). Recently, it has been established that decanoic acid, but not octanoic acid, has anti-seizure effects at clinically relevant concentrations in vitro and in vivo (Chang et al., Neuropharmacology 2013; 69: 105-114; Wlaz et al., Progress in Neuropsychopharmacology & Biological Psychiatry 2014).

a-amino-3-hydroxy-5-methyl-4-isoxazolepropionic acid receptors (AMPA receptors) play a key role in generating and propagating epileptic activity and in the long-term, adaptive cellular plasticity associated with epileptogenesis (Chapman, J Nutr 2000; 130: 1043S-1045S; Rogawski and Donevan, Adv Neurol 1999; 79: 947-963). The receptors are present in all areas relevant to epilepsy, including the cerebral cortex, amygdala, thalamus and hippocampus.

Furthermore, AMPA receptor antagonists have a broad spectrum of anticonvulsant activity in various in vitro and in vivo epilepsy models ((Rogawski., Epilepsy Curr 2011; 11: 56-63). The noncompetitive AMPA receptor antagonist perampanel has been approved in the treatment of adults with partial seizures (French et al., 2012 Neurology. 79 (6): 589-96).

We have recently demonstrated that decanoic acid inhibits AMPA receptors and that the degree of AMPA receptor antagonism of decanoic acid is sufficient to explain its anti-seizure effect (Chang et al., Brain. 2016 February; 139(2): 431-443). In contrast, octanoic acid had no effect on AMPA receptor currents suggesting that octanoic acid is unlikely to have a direct effect on seizure control through AMPA receptor inhibition.

To facilitate the further development of anti-convulsive medication, there remains a need to further understand the contribution of medium chain fatty acids on the alleviation of epileptic seizures.

SUMMARY OF THE INVENTION

We investigated the effect of mixtures of decanoic acid and octanoic acid on AMPA receptor inhibition. Although previous studies have suggested that decanoic acid and not octanoic acid was unlikely to have a direct effect on AMPA receptor mediated seizure control, we surprisingly found that maximal AMPA receptor inhibition was established when combining decanoic acid and octanoic acid at specific ratios referred to herein.

We further demonstrated that decanoic acid and octanoic acid are differentially metabolised by neuronal-like cells. Moreover, octanoic acid may be preferentially oxidised thereby sparing decanoic acid from being oxidised.

STATEMENTS OF THE INVENTION

According to a first aspect of the present invention there is provided a composition comprising a decanoic acid to octanoic acid ratio of 70:30 to 90:10 wt/wt for use in treating epilepsy.

According to another aspect of the present invention there is provided a composition comprising a decanoic acid to octanoic acid ratio of 70:30 to 90:10 wt/wt for use in controlling epileptic seizures.

According to another aspect of the present invention there is provided a composition comprising a decanoic acid to octanoic acid ratio of 70:30 to 90:10 wt/wt for use in reducing excitatory post-synaptic currents (EPSCs) in a subject with epilepsy.

According to another aspect of the present invention there is provided a composition comprising a decanoic acid to octanoic acid ratio of 70:30 to 90:10 wt/wt for use in inhibiting AMPA receptors in a subject in need of said inhibition. Said subject may be suffering from epilepsy. According to another aspect of the present invention said subject may be suffering from ischemia, amyotrophic lateral sclerosis (ALS), cancer or Alzheimer's Disease.

According to another aspect of the present invention there is provided a composition comprising a decanoic acid to octanoic acid ratio of 70:30 to 90:10 wt/wt for use in treating ischemia.

According to another aspect of the present invention there is provided a composition comprising a decanoic acid to octanoic acid ratio of 70:30 to 90:10 wt/wt for use in treating amyotrophic lateral sclerosis (ALS).

According to another aspect of the present invention there is provided a composition comprising a decanoic acid to octanoic acid ratio of 70:30 to 90:10 wt/wt for use in treating cancer.

According to another aspect of the present invention there is provided a composition comprising a decanoic acid to octanoic acid ratio of 70:30 to 90:10 wt/wt for use in treating Alzheimer's Disease (AD).

According to another aspect of the present invention there is provided a composition for use in treating epilepsy or controlling seizures in a subject wherein the subject has been identified as a subject that would respond to AMPA receptor inhibition.

The composition for use in the invention may comprise a decanoic acid to octanoic acid ratio of 70:30 to 90:10, 71:29 to 89:11, 72:28 to 88:12, 73:27 to 87:13, 74:26 to 86:14, 75:25 to 85:15, 76:24 to 84:16, 77:23 to 83:17, 78:22 to 82:18 or 79:21 to 81:19 wt/wt.

Preferably, the composition for use in the invention comprises a decanoic acid to octanoic acid ratio of about 80:20 wt/wt.

The decanoic acid and octanoic acid referred to herein may be in the form of triglycerides.

In one embodiment, the octanoic acid and decanoic acid make up at least 80, 85, 90, 95 or 99%, or 100% by weight of the total fatty acid content of the composition. In one embodiment, the octanoic acid and decanoic acid are in the form of medium chain triglycerides wherein said triglycerides make up at least 80, 85, 90, 95 or 99%, or 100% of the total fat content of the composition. Preferably, substantially all the fatty acid moieties of the MCTs are octanoic or decanoic acid moieties.

In another embodiment, the composition for use in the invention is substantially free of mono- or poly-unsaturated fatty acids.

In another embodiment, the composition for use in the invention is in the form of an oil-in-water emulsion, a powder or a food stuff.

In another embodiment, the composition for use in the invention is in liquid form wherein the decanoic acid is present at 5 g/l to 500 g/l, 5 g/l to 200 g/l, 5 g/l to 100 g/l, 5 g/l to 50 g/l, 5 g/l to 30 g/l, 5 g/l to 20 g/l, 10 g/l to 500 g/l, 10 g/l to 200 g/l, 10 g/l to 100 g/l, 10 g/l to 50 g/l, 10 g/l to 30 g/l or 10 g/l to 20 g/l.

For example, decanoic acid may be present at about 5 g/l, about 10 g/l, about 15 g/l, about 20 g/l, about 30 g/l, about 40 g/l, about 50 g/l, about 60 g/l, about 70 g/l, about 80 g/l, about 90 g/l, about 100 g/l, about 110 g/l, about 120 g/l, about 130 g/l, about 140 g/l, about 150 g/l, about 175 g/l, about 200 g/l, about 225 g/l, about 250 g/l or about 500 g/l.

In another embodiment, the composition for use in the invention is free, or substantially free, of carbohydrate and protein, e.g. the composition has less than 2%, 0.5% or 0.1% carbohydrate and protein by weight.

In another embodiment, the weight amounts of lipid to the sum of proteins and carbohydrates in the composition is 1-5 to 1. For example, the weight amounts of lipid to the sum of proteins and carbohydrates may be 1 to 1, 2 to 1, 3 to 1, 4 to 1, 5 to 1, 2.4-4.0 to 1, or 2.6-3.8 to 1.

The composition may be in the form of an oil-in-water emulsion. In one embodiment, the emulsion comprises octanoic acid and decanoic acid in the form of medium chain triglycerides wherein said medium chain triglycerides make up at least 80, 85, 90, 95 or 99%, or 100% of the total fat content of the composition. Preferably, all, or substantially all, of the fatty acid moieties of the MCTs are octanoic or decanoic acid moieties. The emulsion may comprises substantially no protein or carbohydrate. In one embodiment, the total fat content of the oil in water emulsion is 5 to 40 g/100 ml, for example 5 to 30 g/100 ml, 5 to 25 g/100 ml, 10-25 g/100 ml or 10-20 g/100 ml or 15 to 25 g/100 ml. In one embodiment, the energy value of the emulsion is between 50 to 300 kcal per 100 ml, for example, 100 to 300 kcal per 100 ml, 50 to 200 kcal per 100 ml, 150 to 250 kcal per 100 ml or 170 to 200 kcal per 100 ml.

In one embodiment, the composition used in the invention is in powdered form.

In another embodiment, the composition is in a spray dried form.

In another embodiment, the composition is in a form suitable for fortifying food or drink.

In another embodiment, the composition is in the form of a food stuff.

In another embodiment, the composition is in the form of a medical food.

In another embodiment, the composition is in the form of a tube feed.

The composition for use in the invention may be in the form of a beverage, mayonnaise, salad dressing, margarine, low fat spread, dairy product, cheese spread, processed cheese, dairy dessert, flavoured milk, cream, fermented milk product, cheese, butter, condensed milk product, ice cream mix, soya product, pasteurised liquid egg, bakery product, confectionary product, confectionary bar, chocolate bar, high fat bar, UHT pudding, pasteurised pudding, gel, jelly, yoghurt, or a food with a fat-based or water-containing filling.

According to another aspect of the present invention there is provided use of octanoic acid for reducing or preventing neuronal oxidation of decanoic acid.

According to another aspect of the present invention there is provided octanoic acid for use in reducing or preventing neuronal oxidation of decanoic acid.

According to another aspect of the present invention there is provided octanoic acid for use in reducing or preventing neuronal oxidation of decanoic acid wherein the decanoic acid is for use in treating epilepsy.

According to another aspect of the present invention there is provided octanoic acid for use in reducing or preventing neuronal oxidation of decanoic acid wherein the decanoic acid is for use in controlling epileptic seizures.

According to another aspect of the present invention there is provided octanoic acid for use in reducing or preventing neuronal oxidation of decanoic acid wherein the decanoic acid is for use in inhibiting AMPA receptors in a subject in need of said inhibition. Said subject may be suffering from epilepsy. According to another aspect of the present invention said subject may be suffering from ischemia, amyotrophic lateral sclerosis (ALS), cancer or Alzheimer's Disease.

According to another aspect of the present invention there is provided octanoic acid for use in reducing or preventing neuronal oxidation of decanoic acid wherein the decanoic acid is for use in treating ischemia.

According to another aspect of the present invention there is provided octanoic acid for use in reducing or preventing neuronal oxidation of decanoic acid wherein the decanoic acid is for use in treating amyotrophic lateral sclerosis (ALS).

According to another aspect of the present invention there is provided octanoic acid for use in reducing or preventing neuronal oxidation of decanoic acid wherein the decanoic acid is for use in treating cancer.

According to another aspect of the present invention there is provided octanoic acid for use in reducing or preventing neuronal oxidation of decanoic acid wherein the decanoic acid is for use in treating Alzheimer's Disease (AD).

According to another aspect of the present invention there is provided a method of treating epilepsy in a subject wherein said method comprises administering to the subject a composition as defined herein.

According to another aspect of the present invention there is provided a method of controlling epileptic seizures in a subject wherein said method comprises administering to the subject a composition as defined herein.

According to another aspect of the present invention there is provided a method of reducing excitatory post-synaptic currents (EPSCs) in a subject with epilepsy wherein said method comprises administering to the subject a composition as defined herein.

According to another aspect of the present invention there is provided a method of inhibiting AMPA receptors in a subject comprising administering to the subject a composition as defined herein. Said subject may be suffering from epilepsy.

DETAILED DESCRIPTION

Composition

Figure 1:
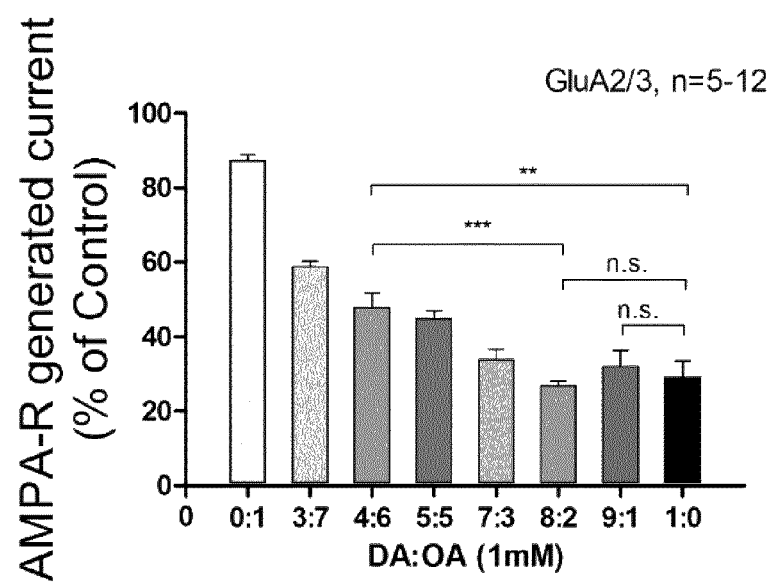
FIG. 1. Direct inhibition of AMPA receptor generated currents by application of blended decanoic acid and octanoic acid. Experiments used GluA2/3 AMPA receptors, expressed in the oocyte model, with the addition of 100 uM glutamate. Ratios of decanoic acid to octanoic acid were assessed for inhibitory effect. A highly significant increase in inhibition was shown for 8:2 ratio compared to 4:6. $P>0.01$, *$P>0.001$, n.s=non-significant.

The present invention makes use of compositions comprising decanoic (C10) acid and octanoic acid (C8).

Octanoic acid (also known as caprylic acid) is a saturated fatty acid of the formula $CH_3(CH_2)_6COOH$.

Decanoic acid (also known as capric acid) is a saturated fatty acid of the formula $CH_3(CH_2)_8COOH$.

The composition used in the present invention comprises a decanoic acid to octanoic acid ratio of 70:30 to 90:10 wt/wt.

The composition may comprise a decanoic acid to octanoic acid ratio of 71:29 to 89:11, 72:28 to 88:12, 73:27 to 87:13, 74:26 to 86:14, 75:25 to 85:15, 76:24 to 84:16, 77:23 to 83:17, 78:22 to 82:18, 79:21 to 81:19 wt/wt.

In a preferred embodiment composition may comprise a decanoic acid to octanoic acid ratio of 75:25 to 85:15, preferably 76:24 to 84:16, 77:23 to 83:17, 78:22 to 82:18, in a preferred embodiment the ratio of 79:21 to 81:19 wt/wt.

The composition may comprise a decanoic acid to octanoic acid ratio of about 70:30, about 71:29, about 72:28, about 73:27, about 74:26, about 75:25, about 76:24, about 77:23, about 78:22, about 79:21, about 80:20, about 81:19, about 82:18, about 83:17, about 84:16, about 85:15, about 86:14, about 87:13, about 88:12, about 89:11 or about 90:10. In a preferred embodiment, the ratio is about 80:20 wt/wt.

Preferably the octanoic acid and decanoic acid make up at least 80, 85, 90, 95 or 99%, or 100% of the total fatty acid content of the composition.

It will be appreciated that the decanoic acid and octanoic acid may be in free form (or a salt thereof) or in the form of, for example, triglycerides, diacyl-glycerides, monoacyl-glycerides, with triglycerides being generally preferred.

A medium-chain triglyceride (MCT) is a triglyceride in which all three fatty acid moieties are medium-chain fatty acid moieties. As defined herein, medium-chain fatty acids (MCFA) are fatty acids that have 6 to 12 carbon atoms, although fatty acids with 8 and 10 carbon atoms (i.e. octanoic acid and decanoic acid) are particular preferred in the present invention and are referred to herein as C8 fatty acids or C8, and C10 fatty acids or C10.

The term "fatty acid moiety" refers to the part of the MCT that originates from a fatty acid in an esterification reaction with glycerol. In one example, an esterification reaction between glycerol and only octanoic acid would result in a MCT with octanoic acid moieties. In another example, an esterification reaction between glycerol and only decanoic acid would result in a MCT with decanoic acid moieties.

The composition used in the invention may comprise homotriglycerides (i.e. all of the fatty acid moieties of the MCT are of the same identity, for example a C8 homotriglyceride may comprise 3 octanoic acid moieties and a C10 homotriglyceride may comprise 3 decanoic acid moieties). The composition may comprise heterotriglycerides (i.e. the fatty acid moieties of the MCT are not all the same identity).

In one embodiment, the composition is free from or substantially free from fatty acid moieties that are not octanoic acid or decanoic acid. In one embodiment, the composition is free from or substantially free from MCTs comprising fatty acid moieties that are not octanoic acid or decanoic acid. However, there may be traces of such MCTs (e.g., less than 3, 2, 1 or 0.5 wt %).

Examples of natural sources of MCT include plant sources such as coconuts, coconut oil, palm kernels, palm kernel oils, and animal sources such as milk. Decanoic acid and octanoic acid form about 5-8% and 4-10% of the fatty acid composition of coconut oil, respectively.

MCTs may also be synthesised by esterification of glycerol with one or more medium-chain fatty acids (MCFA). For example, MCT-C8 can be synthesised by esterification of glycerol with octanoic acid and MCT-C10 can be synthesised by esterification of glycerol with decanoic acid.

The present invention may utilise long chain triglycerides (LCTs). Preferably the LCTs are at a level of 5%, 2%, 1%, 0.5% or 0.1 wt %. In one embodiment, no LCTs are present in the composition.

The composition may further comprise substances such as minerals, vitamins, salts, functional additives including, for example, palatants, colorants, emulsifiers, antimicrobial or other preservatives. Minerals that may be useful in such compositions include, for example, calcium, phosphorous, potassium, sodium, iron, chloride, boron, copper, zinc, magnesium, manganese, iodine, selenium, chromium, molybdenum, fluoride and the like. Examples of vitamins that may be useful in compositions described herein include water soluble vitamins (such as thiamin (vitamin B1), riboflavin (vitamin B2), niacin (vitamin B3), pantothenic acid (vitamin B5), pyridoxine (vitamin B6), biotin (vitamin B7), myo-inositol (vitamin B8), folic acid (vitamin B9), cobalamin (vitamin B12), and vitamin C) and fat soluble vitamins (such as vitamin A, vitamin D, vitamin E, and vitamin K) including salts, esters or derivatives thereof. Inulin, taurine, carnitine, amino acids, enzymes, coenzymes, and the like may be useful to include in various embodiments.

In one embodiment, the composition is in the form of an oil-in-water emulsion. The emulsion may comprise substantially no protein or carbohydrate. In one embodiment, the total fat content of the oil-in-water emulsion is 5 to 40 g/100 ml, for example 5 to 30 g/100 ml, 5 to 25 g/100 ml, 10-25 g/100 ml or 10-20 g/100 ml or 15 to 25 g/100 ml. In one embodiment, the energy value of the emulsion is between 50 to 300 kcal per 100 ml, for example, 100 to 300 kcal per 100 ml, 50 to 200 kcal per 100 ml, 150 to 250 kcal per 100 ml or 160 to 200 kcal per 100 ml.

In another embodiment the composition is delivered as part of a ketogenic diet. Briefly, the classical version of the ketogenic diet uses ratios to determine and describe fat content. Thus, the ketogenic ratio represents the relationship between the grams of fat and the combined grams of protein and carbohydrate. In a 4:1 ratio there are four times as many grams of fat for every 1 g of protein and carbohydrate combined. The ratio is traditionally intended to regulate the degree of ketosis, with higher ratios theoretically stimulating greater ketosis. The MCT version of the ketogenic diet uses percentage energy from fat to determine and describe fat content. The other two versions of the ketogenic diet are the so-called modified Atkins diet and the low glycaemic (GI) index diet, which encourage people to ingest a lot of fat. In these two latter diets neither the ratio nor the percentage of fat is formally calculated although typically the ketogenic ratio is about 1:1. In all 4 versions of the ketogenic diet the percentage of total energy from fat ranges from 50-92% but is typically 70-90%.

If the invention is delivered as part of a ketogenic diet, the ratio of total fat content: protein/carbohydrate content can be altered during therapy to achieve nutritional goals and to optimise clinical benefit. The ratio can be in the range of, for example 1:1 to 7: 1, 1:1 to 5:1, for example, 1:1, 1.5:1, 2:1, 2.5:1, 3:1, 3.5:1, 4:1, 4.5:1 or 5:1.

In one embodiment the ratio is 2.25:1 to 3.9:1. In another embodiment the ratio is 2.26 to 3.8:1 or 2.7-3.4:1. In further embodiments the ratio is 3.21:1, 3.23:1, 3.24:1, 3.25:1, 3.26:1, 3.27:1, 3.28:1 or 3.29:1.

It should be borne in mind that two different individuals of the same age and weight may experience a different level of clinical benefit on the same ratio or quantity of fat. Thus a clinician may wish to alter the ratio to achieve the optimum clinical benefit. Thus, fine tuning the ratio or total fat content and altering it at the start and end of therapy, and during the therapy, e.g. to increase compliance, is within the scope of the invention.

The composition may be for enteral or parenteral administration. In a preferred embodiment the composition is for oral administration.

In one embodiment the composition of the invention is in the form of a tablet, dragee, capsule, gel cap, powder, granule, solution, emulsion, suspension, coated particle, spray-dried particle or pill.

In another embodiment the composition may be in the form of a powder. The powder may, for example, be a spray-dried powder or a freeze-dried powder.

The composition may be usable for reconstitution in water.

The composition may be inserted or mixed into a food substance. The composition may be in the form of a food stuff or a feed. In one embodiment the food stuff is a human food stuff.

The composition may be in the form of a medical food. The term "medical food" as used herein refers to a food product specifically formulated for the dietary management of a medical disease or condition; for example, the medical disease or condition may have distinctive nutritional needs that cannot be met by normal diet alone. The medical food may be administered under medical supervision. The medical food may be for oral ingestion or tube feeding.

The composition may be in the form of a tube feed. The term "tube feed" refers to a product which is intended for introducing nutrients directly into the gastrointestinal tract of a subject by a feeding tube. A tube feed may be administered by, for example, a feeding tube placed through the nose of a subject (such as nasogastric, nasoduodenal, and nasojejunal tubes), or a feeding tube placed directly into the abdomen of a subject (such as gastrostomy, gastrojejunostomy, or jejunostomy feeding tube).

The composition may be in the form of a nutritional composition or a nutritional supplement. The term "nutritional supplement" refers to a product which is intended to supplement the general diet of a subject.

The composition may be in the form of a complete nutritional product. The term "complete nutritional product" refers to a product which is capable of being the sole source of nourishment for the subject.

In various embodiments the composition may be in the form of a beverage, mayonnaise, salad dressing, margarine, low fat spread, dairy product, cheese spread, processed cheese, dairy dessert, flavoured milk, cream, fermented milk product, cheese, butter, condensed milk product, ice cream mix, soya product, pasteurised liquid egg, bakery product, confectionary product, confectionary bar, chocolate bar, high fat bar, liquid emulsion, spray-dried powder, freeze-dried powder, UHT pudding, pasteurised pudding, gel, jelly, yoghurt, or a food with a fat-based or water-containing filling.

In yet other embodiments the composition of the invention may be used to coat a food.

The composition may in the form of a pharmaceutical composition and may comprise one or more suitable pharmaceutically acceptable carriers, diluents and/or excipients.

Examples of such suitable excipients for compositions described herein may be found in the "Handbook of Pharmaceutical Excipients, 2nd Edition, (1994), Edited by A Wade and PJ Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s) and/or solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption and that are used as standard in the food industry. Typical nutritionally acceptable carriers, diluents and excipients will be familiar to the skilled person in the art.

AMPA Receptors

AMPA receptors are glutamate-gated cation channels that mediate the majority of fast excitatory transmission in the brain. They are ligand-gated ion channels composed of combinations of four separate subunits (GluA1-4). Most AMPA receptors are heterotetrameric, consisting of symmetric 'dimer of dimers' of GluR2 and either GluR1, GluR3 or GluR4. AMPA receptors are highly mobile proteins that undergo constitutive and activity-dependent translocation to, recycling at, and removal from, synapses (Henley et al., Trends Neurosci. 2011; 34:258-268; Anggono et al., Curr Opin Neurobiol. 2012; 22:461-469). All subunits share a common membrane topology with each other, and with NMDAR and kainate receptor subunits.

Each AMPA receptor has four sites to which an agonist (such as glutamate) can bind, one for each subunit. The binding site is believed to be formed by the N-terminal tail and the extracellular loop between transmembrane domains three and four. When an agonist binds, these two loops move towards each other, opening the pore. The channel opens when two sites are occupied, and increases its current as more binding sites are occupied. Once open, the channel may undergo rapid desensitisation, stopping the current. AMPA receptors open and close quickly (1 ms), and are thus responsible for most of the fast excitatory synaptic transmission in the central nervous system.

Inhibitors of AMPA receptor reduce excitatory post-synaptic currents (EPSCs). Decanoic acid has been shown to decrease such currents and has been shown to be an inhibitor of the AMPA receptor (Chang et al., Brain. 2016 February; 139(2): 431-443).

Owing to the ability of the compositions referred to herein to optimally inhibit the AMPA receptor, the compositions can be used to inhibit AMPA receptors in a subject in need of said inhibition. Preferably, said subject suffers from epilepsy.

Treatment

As used herein, the term "treatment" means to administer a composition as described herein to a subject having a condition in order to prevent, lessen, reduce or improve at least one symptom associated with the condition and/or to slow down, reduce or block the progression of the condition.

To "prevent" means to administer a composition as described herein to a subject that is not showing any symptoms of the condition to reduce or prevent development of at least one symptom associated with the condition.

Epilepsy

Epilepsy is a neurological disorder in which nerve cell activity in the brain becomes disrupted, causing seizures or periods of unusual behaviour, sensations and sometimes loss of consciousness.

AMPA receptors play a key role in the generation and spread of epileptic seizures (Rogawski et al., Acta Neural. Scand. Suppl. 127 (197): 9-18). The receptors are present in all areas relevant to epilepsy, including the cerebral cortex, amygdala, thalamus and hippocampus.

Furthermore, AMPA receptor antagonists have a broad spectrum of anticonvulsant activity in various in vitro and in vivo epilepsy models ((Rogawski., Epilepsy Curr 2011; 11: 56-63). The noncompetitive AMPA receptor antagonist perampanel (Fycompa) has been approved for the adjunctive treatment of partial-onset seizures and primary tonic-clonic seizures. Other AMPA receptor antagonists include NBQX (2,3-dihydroxy-6-nitro-7-sulfamoyl-benzo[f]quinoxaline-2, 3-dione).

Owing to the ability of the compositions referred to herein to optimally inhibit the AMPA receptor, the compositions may be used to treat epilepsy.

Amyotrophic Lateral Sclerosis

Amyotrophic lateral sclerosis (ALS), also known as Lou Gehrig's disease and motor neurone disease (MND) is the most common adult-onset motor neuron disease, and is characterised by the progressive loss of both upper and lower motor neurons resulting in muscle weakness and atrophy throughout the body. ALS may be inherited or sporadic. Typically, patients with ALS die from progressive respiratory muscle paralysis within a few years after disease onset. Excitotoxicity, a pathological process in which neurons are damaged and killed by over-activity of AMPA receptors, has been proposed to underlie ALS pathogenesis. Orally administered perampanel, a selective, non-competitive AMPA receptor antagonist prevented the progression of the ALS phenotype in a mouse model of ALS (Akamatsu et al., Sci. Rep (2017) 6:28649).

Ischemia

Ischemia is a restriction in blood flow to a tissue associated with a deleterious shortage in oxygen and glucose supply, e.g. hypoxia and hypoglycaemia. During ischemia, the $Ca^2+$permeability of AMPA receptors may increase, which can lead to excitotoxicity and associated neuronal cell death. $Ca^2+$-permeable AMPA receptors have been shown to be highly expressed in CA1 pyramidal neurons—a region of the hippocampus that is more vulnerable to cell death following an ischemic event than other hippocampal regions. AMPA receptor antagonists, such as NBQX, have been demonstrated to be beneficial in preventing neuronal loss in animal models of ischemia (Chang et al., (2012) European Journal of Neuroscience, 35, 1908-1916).

Cancer

A link between the MCT ketogenic diet, AMPA receptors and cancer treatment has been established by studies demonstrating that human glioblastoma cells express increased levels of AMPA receptors (Choi, J., et al., Glioblastoma cells induce differential glutamatergic gene expressions in human tumor-associated microglia/macrophages and monocyte-derived macrophages. Cancer Biol Ther, 2015. 16(8): p. 1205-13), and inhibition of AMPA receptors suppresses migration and proliferation of glioblastoma multiforme cells (GBM) (Ishiuchi, S., et al., Ca2+-permeable AMPA receptors regulate growth of human glioblastoma via Akt activation. J Neurosci, 2007. 27(30): p. 7987-8000, Ishiuchi, S., et al., Blockage of Ca(2+)-permeable AMPA receptors suppresses migration and induces apoptosis in human glioblastoma cells. Nat Med, 2002. 8(9): p. 971-8, Yoshida, Y., et al., Serum-dependence of AMPA receptor-mediated proliferation in glioma cells. Pathol Int, 2006. 56(5): p. 262-71.) and other cancer cells (von Roemeling, C. A., et al., Neuronal pentraxin 2 supports clear cell renal cell carcinoma by activating the AMPA-selective glutamate receptor-4. Cancer Res, 2014. 74(17): p. 4796-810). Furthermore, the recently licensed AMPA receptor-specific inhibitor Perampanel has been shown to be a potentially chemotherapeutically active adjuvant in a single case study of GBM treatment (Rasche, J., et al., [Perampanel in the treatment of a patient with glioblastoma multiforme without IDH1 mutation and without MGMT promotor methylation]. Fortschr Neural Psychiatr, 2015. 83(5): p. 286-9.) These studies thus suggest that AMPA receptor inhibition through decanoic acid has potential to provide an adjunctive cancer treatment.

Alzheimer's Disease

There is strong evidence that amyloid f3 (Af3) increases AMPA receptor currents and triggers subunit internalization, a theory that directly links glutamate receptor hyperactivity to neurotoxicity and memory loss in Alzheimer's disease. Af3 has been shown to interact with f3 adrenergic receptors which regulate gene expression and the activity of various receptors including AMPA-type glutamate receptors via the cAMP/PKA signaling cascade (Wang, D., et al., Binding of amyloid beta peptide to beta2 adrenergic receptor induces PKA-dependent AMPA receptor hyperactivity. FASEB J, 2010. 24(9): p. 3511-21, Wisely, E. V., Y. K. Xiang, and S. Oddo, Genetic suppression of beta2-adrenergic receptors ameliorates tau pathology in a mouse model of tauopathies. Hum Mol Genet, 2014. 23(15): p. 4024-34). Phosphorylation of AMPA receptor GluA1 subunits by PKA has been shown to increase channel opening probability which results in augmented calcium entry into the cell (Banke, T. G., et al., Control of GluR1 AMPA receptor function by cAMP-dependent protein kinase. J Neurosci, 2000. 20(1): p. 89-102). Indeed, numerous studies have shown that the addition of AI3 to neuronal cultures causes neurotoxicity by strengthening calcium-dependent AMPA-receptor generated currents (Whitcomb, D. J., et al., Intracellular oligomeric amyloid-beta rapidly regulates GluA1 subunit of AMPA receptor in the hippocampus. Sci Rep, 2015. 5: p. 10934). This suggests that AI3 induced excitotoxicity could contribute to the widespread neuronal death in Alzheimer's disease. In addition to ketones providing energy to glucose resistant neurons, the MCT ketogenic diet might therefore improve neuronal survival through the inhibition of AMPA receptors by decanoic acid. In addition, there is evidence that AJ3 treatment triggers the internalization of GluA2 subunits, the only AMPA receptor subunit type that confers calcium impermeability. Internalization of GluA2 could therefore further increase total calcium influx at the post-synapse which could further increase inflammation and neurotoxicity (Beppu, K., et al., Expression, subunit composition, and function of AMPA-type glutamate receptors are changed in activated microglia; possible contribution of GluA2 (GluR-B)-deficiency under pathological conditions. Glia, 2013. 61(6): p. 881-91, Noda, M., Dysfunction of Glutamate Receptors in Microglia May Cause Neurodegeneration. Curr Alzheimer Res, 2016. 13(4): p. 381-6) suggesting a role for AMPA receptor antagonists in the treatment of Alzheimer's disease.

Administration

The compositions as described herein may be administered enterally or parenterally.

Preferably, the composition is administered enterally. For example, the composition may be administered in the form of a food stuff or a supplement.

Enteral administration may be oral, gastric, and/or rectal.

In general terms, administration of the composition as described herein may, for example, be by an oral route or another route into the gastro-intestinal tract, for example the administration may be by tube feeding.

The subject may be a mammal such as a human, canine, feline, equine, caprine, bovine, ovine, porcine, cervine and primates. Preferably the subject is a human.

EXAMPLES

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *ONA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: ONA Structure Part A: Synthesis and Physical Analysis of ONA Methods in Enzymology*, Academic Press; and E. M. Shevach and W. Strober, 1992 and periodic supplements, *Current Protocols in Immunology*, John Wiley & Sons, New York, N.Y. Each of these general texts is herein incorporated by reference.

Example 1—Effect of Decanoic Acid:Octanoic Acid Ratio Treatment on Electrophysiological Recordings from Oocytes Methods In Vitro RNA Transcription of AMPA Receptor Subunits The AMPA receptor (flip isoform) cDNAs inserted in a SP6 polymerase expression vector (pSP6T) were a gift from Prof Ralf Schoepfer (NPP, UCL). RNA was transcribed in vitro from Miu I linearised transcripts using the SP6 Promega RiboMax RNA synthesis kit (Madison, Wis.) according to manufacturers protocols except for the addition of 0.75 mM capping nucleotide m7G(5')ppp(5')G (Promega, Madison, Wis.) and 1.6 mM GTP. cRNA concentrations and integrity were estimated by the intensity of fluorescence bands in RNA denaturating gels. AMPA receptor cRNAs were mixed in a nominal 1:1 ratio and approximately 5 ng was injected per oocyte.

Oocyte Preparation and Injection

*Xenopus laevis* oocytes were purchased from the European *Xenopus* Resource Centre, University of Portsmouth. Stage V to VI oocytes were mechanically dissected and then subjected to gentle shaking for approximately 30-50 min at room temperature with modified Barth's solution (in mM): NaCl 88, KCl 1, $NaHCO_3$ 2.4, $MgCb$ 0.82, $CaCl_2$) 0.77, Tris-Cl 15, adjusted to pH 7.4 with NaOH (Sigma-Aldrich, UK), supplemented with 50 IU/ml penicillin and 50 µg/ml streptomycin (Invitrogen, UK) and 50 µg/ml tetracycline (Sigma-Aldrich, UK) and 1% collagenase (type 1A). Healthy oocytes were manually defolliculated and the injections of cRNA for homomeric subunits alone (GluA1), or heteromeric mixtures of two subunits together (GluA2/GluA3) were made using an automated Drummond Nanoinject II injector (Broomall, Pa.). The oocytes were then incubated at 17° C. in modified Barth's solution for at least 48 hours before use in electrophysiological recordings.

Electrophysiological Recordings from Oocytes

Experiments were performed at room temperature (approximately 21-23° C.). An oocytewas placed in a recording chamber (0.3-0.5 ml volume) and perfused with ND96 solution (96 mM NaCl, 2 mM KCl, 1.8 mM CaCb, 1 mM MgCb, 5 mM HEPES, with pH adjusted to 7.5). Current and voltage electrodes were filled with 300 mM KCl and made from thin-walled borosilicate glass (GC150TF-7.5, Harvard Apparatus, Kent, UK) using a PC-10 electrode puller (Narashige Instruments, Japan) and had resistances of 0.5-2 MO. Oocytes were voltage-clamped to a holding potential of –50 mV or –60 mV using a Turbo TEC-03 amplifier (npi electronics, Tamm, Germany). Compounds were dissolved in distilled water or DMSO and dissolved in bathing solution to achieve their final concentrations during experiments, and were applied under gravity flow during the experiment by using a multi-valve perfusion system (VC3-8C, ALA Scientific Instruments, Farmingdale, N.Y.). The bath solutions were perfused at a rate of 10 ml/min. Recordings were filtered at 20 Hz and digitized at 100 Hz (Digidata 1322A, Molecular Devices, Sunnyvale, Calif.) before recording to computer hard disk. Data acquisition was performed using the Windows PC based programme, WinEDR v3.0.6 (John Dempster, University of Strathclyde, UK).

Results

We have previously shown that decanoic acid has acute antiseizure effects and that AMPA receptor antagonism of decanoic acid is sufficient to explain its antiseizure effect (Chang et al., Neuropharmacology 2013; 69: 105-114); Wlaz et al., Progress in Neuropsychopharmacology & Biological Psychiatry 2014).

Our previous studies had identified decanoic acid as a direct inhibitor of AMPA receptor activity (GluA 2/3; IC50=0.52±0.02 mM, n=12); octanoic acid has a similar but less potent effect (GluA 2/3; IC50=3.82±0.03 mM, n=10). We demonstrated that this inhibition is likely to lead to seizure control, since the concentration of decanoic acid in peripheral blood is around to 87-552 µM with an average of 157 µM and octanoic acid is around 104-859 µM, averaging around 306 µM. Furthermore, the ratio of decanoic acid in blood plasma to brain in animal models is around 0.7 suggests that decanoic acid is likely to be present in the brain at concentrations producing AMPA receptor inhibition. Intriguingly, octanoic acid in these experiments is unlikely to have a direct effect on seizure control through AMPA receptor inhibition.

We therefore investigated the effect of both fatty acids on AMPA receptor inhibition, as a mixture, to recapitulate the approximate dosing provided in MCT-related diets. In these experiments, we expressed AMPA receptors (GluA 2/3) in the oocyte model, and compared the reduction in AMPA receptor currents following glutamate administration using ratios of decanoic acid to octanoic acid of 0:1, 3:7, 4:6. 5:5, 6:4, 7:3, 8:2, 9:1, and 1:0 with a total medium chain fatty acid content of 1 mM (FIG. 1). These experiments showed that increasing the ratio of decanoic acid to octanoic acid, enhanced the inhibition of AMPA receptors, at ratios of inhibition up to 8:2 (decanoic acid:octanoic acid). At this ratio (8:2) AMPA receptor inhibition was significantly increased over 4:6 ratio, commonly used in current MCT oils. At ratios above 8:2 (i.e. 9:1 and for only decanoic acid (1:0)), no increase in AMPA receptor inhibition was shown. These data suggest that maximal AMPA receptor inhibition by combining decanoic acid and octanoic acid is provided by an 8:2 ratio Example 2—Comparison of Neuronal Decanoic Acid Oxidation with Neuronal Decanoic Acid Octanoic Acid Oxidation Methods Cell Culture SH-SY5Y cells were utilised between passages 20-24 for all experimental procedures. Cells were cultured in 1:1 Dulbecco's Modified Eagle's Medium (DMEM)/F12 media, containing 17.5 mM glucose and supplemented with 100 ml/L heat-inactivated foetal bovine serum (FBS) and 10 ml/L 200 mM L-glutamine. All cells were maintained in a humidified atmosphere at 37° C. and 5% CO2. Cells were sub-cultured by washing with 10 ml/flask $Mg^{2+}$1c a $^{2+}$-free Dulbecco's phosphate-buffered saline (DPBS), lifted with 2 ml 0.25% trypsin-EDTA and suspended in 8 ml culture medium to inactivate the trypsin. The cell suspension was transferred to a falcon tube and centrifuged for 4 minutes at 500×g. The supernatant was removed and cells suspended in a known volume of fresh culture medium. Cells were counted using the Trypan Blue exclusion test for viability. A known volume of the cell suspension was mixed 1:1 with 0.4% Trypan Blue solution and counted with a Bio-Rad TC20™ Automated Cell Counter (Hemel Hempstead, UK). Cells were then seeded at a density of $1\times10^4$ cells/cm$^2$ in 6-well plates, made up to a final volume of 2 ml with fresh media and cultured for 5 days prior to all experiments. The same starting number of cells was used for each investigation. Media was refreshed every two days.

Glucose, Decanoate and Octanoate Oxidation in SH-SY5Y Cells

All experimental procedures were carried out with the use of a specifically formulated DMEM media, containing a final concentration of 15 mM HEPES, 2.9 mM sodium bicarbonate, 2 mM L-glutamine, 0.5 mM sodium pyruvate and 21.5 µM phenol red. A stock solution of 134.3 mM [U-$^{13}$C] gluco se was prepared by dissolving glucose in DMEM solution and then frozen at –20° C. in aliquots. Stock solutions of 50 mM [1-$^{13}$C] decanoic acid ([1-$^{13}$C] C10) and 50 mM [1-13C]C8 were prepared in DMSO, sterile-filtered and then stored in aliquots at –20° C.

On day 5 of culture, complete growth media was removed and cells washed once with DPBS. Cells were then incubated with 2 ml of the DMEM formula, supplemented with 10% FBS and 3 mM D-glucose, for 20 h at 37° C. and 5% CO2. After 20 h, the media was removed and cells washed once with DPBS. To each well, 3 ml of DMEM was then added containing 3 mM [U-13C]-glucose and vehicle control DMSO, or 3 mM D-glucose with either 250 µM [1-$^{13}$C] C10 or 250 µM [1-$^{13}$C]C8. Wells were then sealed with a 3 ml layer of heavy mineral oil in order to prevent gas exchange between the media and the atmosphere and loss of $^{13}$CO2. Cells were incubated at 37° C. for 6 hours, with 100 µl of media sampled from each well at hourly intervals. Sampled media were immediately stored in rubber-sealed Exetainer™ vials (Labco Ltd, Ceredigion, UK) and kept at –20° C. until analysis.

C10 and CB Co-Incubation

The effects of co-incubating C10 and C8 on C10 oxidation in SH-SY5Y cells were also explored. Additional stock solutions of 25 mM C8 and 100 mM [1-$^{13}$C]C10 were prepared in DMSO, sterile-filtered and stored in aliquots at −20° C. Cells were cultured and incubated for 20 h in 10% FBS-supplemented DMEM media containing 3 mM D-glucose, as previously described. Media was then removed and cells washed. Media was then replaced with 3 ml DMEM containing either 3 mM [U-$^{13}$C]glucose and vehicle control DMSO, or 3 mM unlabelled D-glucose. In each D-glucose-supplemented well, cells were treated with either a final concentration of 250 μM [1-$^{13}$C] C10, or 250 μM [1-$^{13}$C] C10 plus 62.5 μM C8, at a fixed total volume. Wells were then sealed with heavy mineral oil, cells incubated and media sampled as previously outlined.

Preparation of [U-$^{13}$CJ-Palmitic Acid

[U-$^{13}$C]palmitic acid was neutralised with 0.35M NaOH and made to a concentration of 17.5 mM in water, before heating to 70° C. until fully dissolved. Fatty acid-free bovine serum albumin (BSA) was then dissolved to a concentration of 3.5 mM in water at 37° C. Swirling gently, [U-13C]-palmitate ([U-$^{13}$C]—C16) was then slowly added 1:1 to BSA at 37° C., forming an 8.75 mM [U-$^{13}$C] C16:BSA complex (5:1 molar ratio fatty acid:BSA). An additional stock solution of 1.75 mM BSA in water was also prepared. Both solutions were aliquoted and stored at −20° C. until further use.

CPT1 Inhibition Assay

A stock solution of 50 mM etomoxir was prepared in sterile cell culture grade water and stored in aliquots at −20° C. On day 5 of culture, growth medium was replaced with 2 ml DMEM formula containing 3 mM D-glucose and 10% FBS. Cells were incubated with or without the presence of 50 μM etomoxir, for 20 h at 37° C. and 5% CO2. Media were then removed and replaced with 3 ml DMEM, containing 3 mM [U-$^{13}$C] gluco se and vehicle control DMSO or 3 mM D-glucose with either 250 μM [1-$^{13}$C]C10, [1-$^{13}$C] C8 or [U-$^{13}$C] C16:BSA, with 50 μM etomoxir also added to previously exposed cells. Wells were then sealed with heavy mineral oil, with cells incubated and media sampled as previously described.

Measurement of $^{13}$CO2 Release

Samples were thawed at room temperature and 100 μl 1M hydrochloric acid was injected through the septum into each vial to release CO2 from the media. Vials were centrifuged for 30 seconds at 500×g. Samples were then analysed on a GasBench II coupled to a Thermo Delta-XP isotope-ratio mass spectrometer. Ten repeat injections were carried out per sample, with d$^{13}$C/$^{12}$C ratios measured against Vienna Pee Dee Belemnite (VPDB) using a calibrated CO2 reference gas. $^{13}$CO2/$^{12}$CO2 ratios were converted to mole percent excess using absolute molar ratio of $^{13}$C to $^{12}$C (0.0111796) in VPDB. The change in mole percent excess was then converted to nmol CO2 generated using the volume of medium and concentration of bicarbonate (2.9 mM), which was then corrected for the number of labelled carbon atoms (1 for CS and C10, 6 for glucose and 16 for palmitate) to obtain nmol substrate oxidised.

Cell Viability

Cells were incubated for 20 h at 37° C. and 5% CO2 with 50 μM etomoxir in DMEM media supplemented with 10% FBS, and then a further 6 h at 37° C. with 50 μM etomoxir in DMEM media without FBS. Cells were then lifted from wells with 1 ml 0.25% trypsin-EDTA, suspended in 4 ml culture medium and centrifuged for 4 minutes at 500×g. Supernatant was removed and cells suspended in 1 ml of fresh culture medium. Viability of cells was then tested using the Trypan Blue exclusion test.

Statistical Analysis

Data is expressed as mean±SEM, with n number indicating the number of independent experiments carried out. Statistical analysis between two groups was performed using a Student's t-test, where p<0.05 was considered statistically significant.

Results

Oxidation Rates of Glucose, CB and C10 in SHSY5Y Cells $^{13}$C-labelled compounds permit the measurement of cellular oxidation rates of glucose, C8 or C10 via CO2 release emanating from pyruvate dehydrogenase activity and/or the TCA cycle. $^{13}$CO2 release over 6 hours was used to determine and quantify the rate of cellular oxidation of each compound. Cells were treated with 3 mM $^{13}$C-labelled glucose, in order to replicate physiological levels observed in patients under the MCT KO. $^{13}$C-labelled C10 and C8 were added separately to a final concentration of 250 μM, this being the concentration of C10, previously determined by us, for optimum effects upon mitochondria and antioxidant status. Furthermore, this replicates the brain concentration achieved following peripheral C10 administration (Hughes et al. 2014; Wlaz et al. 2015). Unlabelled 3 mM glucose was used in the presence of $^{13}$C-labelled C10 and C8.

Figure 2:
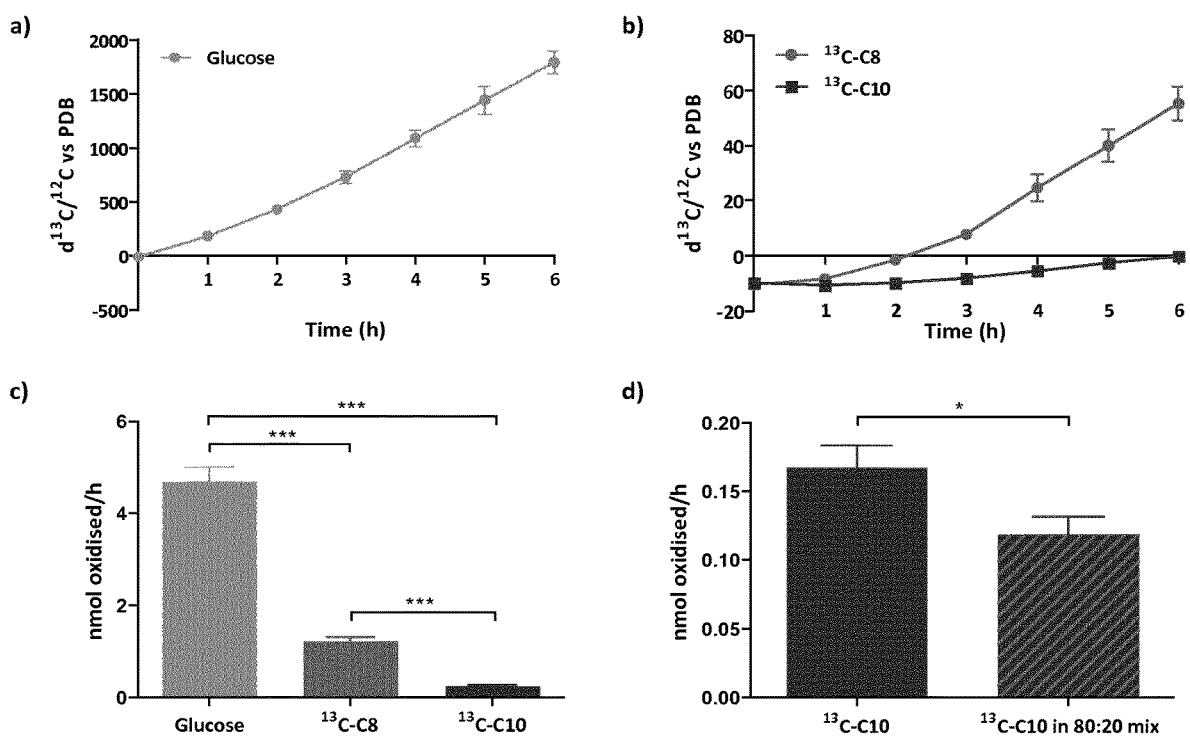
FIG. 2. Oxidation of $^{13}$C-labelled 3 mM glucose, 250 µM C8 and 250 µM C10 in SH-SY5Y cells over the course of 6 h. Rate of $^{13}CO_2$ release into media from cells under (a) 3 mM [U-13C]glucose and (b) 250 µM [1-$^{13}$C] decanoic acid (C10) and [1-$^{13}$C]octanoic acid (C8) treatment, measured by changes in $d^{13}C/^{12}C$ ratio over time. (c) Absolute oxidation rates of $^{13}$C-labelled compounds in SH-SY5Y cells. The oxidation rate of [1-$^{13}$C]C10 was found to be significantly lower (***$p<0.0001$) than that of both [U-$^{13}$C]glucose and [1-$^{13}$C]C8. Data are expressed as mean±SEM of 5 independent experiments (n=5), each performed in 4 replicate wells. (d) Effect of C8 co-incubation on oxidation of C10. The oxidation rate of 250 µM [1-13C]C10 was significantly reduced (*$p<0.05$) in the presence of 62.5 µM unlabelled C8. Data are expressed as mean±SEM of 4 independent experiments (n=4), each performed in 4 replicate wells.

$^{13}$CO2 release, for each molecule studied, was linear for the 6 hour incubation [FIGS. 2a and 2b]. As expected, the rate of glucose concentration was markedly faster than that of either C8 or C10 [FIG. 2c]. However, C8 and C10 were found to be differentially oxidised in these cells, with C10 oxidation significantly lower than that of C8, by approximately 80% (FIG. 2c). This suggests that C8 may be preferentially oxidised in SH-SY5Y cells.

Effect of Co-Incubation of CB and C10 on Oxidation

Current MCT KO preparations are composed of a mixture of C8 and C10. In light of this, we examined the effects on [1-$^{13}$C]C10 oxidation when SH-SY5Y cells were treated 62.5 μM unlabelled C8). Despite the relatively low concentration, C8 addition was found to significantly impair the oxidation rate of C10 by 29% (FIG. 2d, p<0.05).

C10 Oxidation Following CPT1 Inhibition

To determine the mechanisms behind the differential oxidation of C8 and C10, the potential role of the carnitine shuttle was explored. Whilst long chain fatty acids require this system, medium chain fatty acids are generally considered to be able to enter the mitochondrial matrix in a carnitine-independent manner. Whilst this may be the case for C8, there are reports to suggest that C10, in contrast to C8, may require the carnitine system for complete mitochondrial oxidation. Carnitine palmitoyltransferase-1 (CPT1) is responsible fortransferring fatty acyl groups to carnitine and is the rate-limiting step in carnitine-dependent 13-oxidation in mitochondria. To evaluate the potential role of CPT1 in C8 and C10 oxidation, the well-characterised CPT1 irreversible inhibitor, etomoxirwas used. [U-$^{13}$C] palmitic (C16) acid, which is well-known to depend on CPT I for mitochondrial oxidation, was used as a control to allow us to determine the maximal concentration of etomoxir that could be used to inhibit CPT1 without affecting cell viability. With the conditions employed, oxidation of [U-$^{13}$C]C16 was almost completely inhibited, reduced by 99%, suggesting complete irreversible inhibition of CPT1 [Table 1]. Moreover, etomoxir was observed to have no effect on viability of the SH-SY5Y cells used (data not shown). Under the same conditions, C10 oxidation was found to be reduced by 95% in the presence of etomoxir [Table 1], whereas C8 oxidation was only inhibited by 34%.

In conclusion, decanoic acid and octanoic acid are differentially metabolised by neuronal-like cells. The carnitine dependence and sluggish metabolism of C10 provides an explanation for how critical concentrations may occur and permit interaction with key anti-seizure targets. In contrast, C8 may be preferentially metabolised and have two key effects; sparing of C10 by inhibiting C10 oxidation and acting as a fuel source for brain energy metabolism.

| Compound | Oxidation rate (nmol/h) | |
|---|---|---|
| | −Etomoxir | +Etomoxir |
| [1-$^{13}$C]C8 | 1.14 ± 0.11 | 0.75 ± 0.06** |
| [1-$^{13}$C]C10 | 0.20 ± 0.02 | 0.01 ± 0.01*** |
| [U-$^{13}$C]C16 | 0.22 ± 0.05 | 0.002 ± 0.003*** |

Table 1 Effects of CPT1 inhibition on the oxidation rates of C8 and C10 in SH-SY5Y cells. CPT1 inhibition resulted in a significant reduction (*$p<0.0001$ compared with untreated cells) in C10 oxidation by 95%. The oxidation rate of C8 was also significantly reduced by 34% ($p<0.01$ compared to untreated cells). Results are expressed as mean±SEM of 5 independent experiments (n=S), each performed in duplicate. CPT1 inhibition was confirmed with a significant 99% inhibition of [U-$^{13}$C]C16 oxidation (***$p<0.0001$ compared to untreated cells). Results are expressed as mean±SEM of 3 independent experiments (n=3), each performed in duplicate.

The invention claimed is:

1. A method of treating epilepsy or controlling epileptic seizures in an individual in need thereof, the method comprising administering to the individual a composition comprising a decanoic acid to octanoic acid ratio of 71:29 to 89:11 wt/wt.

2. The method according to claim 1, wherein the decanoic acid to octanoic acid ratio is 80:20 wt/wt.

3. The method according to claim 1, wherein the decanoic acid and the octanoic acid are in a form of triglycerides.

4. The method according to claim 1, wherein the composition is in a form selected from the group consisting of a medical food, a tube feed, a nutritional composition and a nutritional supplement.

5. The method according to claim 1, wherein the octanoic acid and the decanoic acid are at least 80% of a total fatty acid content of the composition.

6. The method according to claim 1, wherein the composition further comprises at least one substance selected from the group consisting of minerals, vitamins, salts, preservatives, and combinations thereof.

7. The method according to claim 1, wherein the composition has a total fat content to protein/carbohydrate content ratio of 1:1 to 7:1.

8. A method of reducing excitatory post-synaptic currents (EPSCs) in a subject with epilepsy, the method comprising administering to the subject a composition comprising a decanoic acid to octanoic acid ratio of 71:29 to 89:11 wt/wt.

9. The method according to claim 8, wherein the decanoic acid to octanoic acid ratio is 80:20 wt/wt.

10. The method according to claim 8, wherein the decanoic acid and the octanoic acid are in a form of triglycerides.

11. The method according to claim 8, wherein the composition is in a form selected from the group consisting of a medical food, a tube feed, a nutritional composition and a nutritional supplement.

12. The method according to claim 8, wherein the octanoic acid and the decanoic acid are at least 80% of a total fatty acid content of the composition.

13. A method of inhibiting α-amino-3-hydroxy-5-methyl-4-isoxazolepropionic acid (AMPA) receptors in a subject in need thereof, the method comprising administering to the subject a composition comprising a decanoic acid to octanoic acid ratio of 71:29 to 89:11 wt/wt.

14. The method according to claim 13, wherein the decanoic acid to octanoic acid ratio is 80:20 wt/wt.

15. The method according to claim 13, wherein the decanoic acid and the octanoic acid are in a form of triglycerides.

16. The method according to claim 13, wherein the composition is in a form selected from the group consisting of a medical food, a tube feed, a nutritional composition and a nutritional supplement.

17. The method according to claim 13, wherein the octanoic acid and the decanoic acid are at least 80% of a total fatty acid content of the composition.

* * * * *